United States Patent [19]

Lamparsky et al.

[11] Patent Number: 4,500,729

[45] Date of Patent: Feb. 19, 1985

[54] 2-METHYL-2-BUTEN-1-YL TIGLATE

[75] Inventors: Dietmar Lamparsky, Wangen, Switzerland; Roman Kaiser, Clifton, N.J.

[73] Assignee: Givaudan Corporation, Clifton, N.J.

[21] Appl. No.: 52,175

[22] Filed: Jun. 26, 1979

[30] Foreign Application Priority Data

Jun. 28, 1978 [CH] Switzerland ........................ 7037/78

[51] Int. Cl.[3] ............................................ C07C 69/533

[52] U.S. Cl. ................................ 560/225; 252/522 R; 426/533

[58] Field of Search ......................................... 560/225

[56] References Cited

U.S. PATENT DOCUMENTS 2,164,188 6/1939 Groll et al. .......................... 560/225

OTHER PUBLICATIONS

Buckles, R. E. et al., *Chemical Abstracts,* vol. 44, #9344d, (1950).

Plisov, A. K. et al., *Chemical Abstracts,* vol. 52, #14528h and 14529b, (1958).

Thomas, A. F. et al., *Chemical Abstracts,* vol. 86, #54588s, (1977).

Tsuneya, Tomoyuki et al., "GC–MC Analysis of Gardenia Flower Volatiles", 7th International Congress on Essential Oils, Kyoto, Japan, (1977).

Hattori, Renzo et al., "Chemical Composition of the Absolute from Gardenia Flower", 7th International Congress on Essential Oils, Kyoto, Japan, (1977), *Agric. Biol. Chem.,* vol. 42(7), pp. 1351–1356, (1978).

*Primary Examiner*—Natalie Trousof
*Assistant Examiner*—L. Hendriksen
*Attorney, Agent, or Firm*—Robert F. Tavares

[57] ABSTRACT

The invention is concerned with a novel odorant and/or flavoring substance, namely, 2-methyl-2-buten-1-yl tiglate of the formula

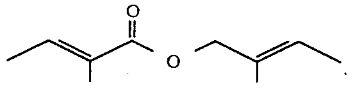

I

The invention is also concerned with a process for the manufacture of the compound of formula I, the compound of formula I as an odorant and/or flavoring substance and odorant and/or flavoring compositions containing the compounds of formula I.

1 Claim, No Drawings

2-METHYL-2-BUTEN-1-YL TIGLATE

FIELD OF THE INVENTION

This invention relates to flavorants and odorants.

SUMMARY OF THE INVENTION

See the foregoing "Abstract of the Disclosure."

The synthetic process provided by the present invention for the manufacture of the compound of formula I comprises esterifying 2-methyl-2-buten-1-ol with tiglic acid or a reactive derivative thereof, or trans-esterifying a tiglic acid lower alkyl ester with 2-methyl-2-buten-1-ol, or reacting a 2-methyl-2-buten-1-yl halide with an alkali metal salt of tiglic acid.

DESCRIPTION OF THE PREFERRED EMBODIMENTS

The esterification of 2-methyl-2-buten-1-ol with tiglic acid or a reactive derivative thereof and the reaction of a 2-methyl-2-buten-1-yl halide with an alkali metal salt of tiglic acid can be carried out according to methods known per se; for example, in accordance with the details given in Table I (see also "Organikum", Org. Chem. Grundpraktikum, VEB Deutscher Verlag der Wissenschaften, Berlin 1969, 9. Edition, p. 440 et seq. or in the 1977 edition, pages 498–506).

TABLE I

| Acid component | Alcohol | Medium | Solvent e.g. | Temp. e.g. |
|---|---|---|---|---|
| Tiglic acid | 2-Methyl-2-buten-1-ol | acidic [0] | Benzene, toluene | 25°–75° C. |
| ~anhydride | 2-Methyl-2-buten-1-ol | basic [2] | Benzene, toluene | " |
| ~halide | 2-Methyl-2-buten-1-ol[1] | " | Benzene, toluene | " |
| ~alkali metal salt | 2-Methyl-2-butene-1-yl halide[3] | neutral | Benzene, toluene | " |

[0] paratoluenesulphonic acid, cation exchanger;
[1] or alcoholate (e.g. sodium or potassium alcoholate);
[2] pyridine, dimethylaniline etc;
[3] especially the chloride.

In the trans-esterification of a tiglic acid lower alkyl ester with 2-methyl-2-buten-1-ol there is preferably used the methyl or ethyl ester, since in this case the low-boiling alcohol methanol or ethanol which is formed can readily be distilled off.

The compound of formula I has particular organoleptic properties, on the basis of which it is excellently suited as an odorant and/or flavouring substance.

The invention is therefore also concerned with the use of the compound of formula I as an odorant and/or flavouring substance.

The compound of formula I used in accordance with the present invention as an odorant and/or flavouring substance possesses an original and, for an ester containing this number of carbon atoms, very surprising odour. This can be described as follows: reminiscent of damp forest soil, fungus-like (mushroom), slightly anis-like, flowery, delicate, with aspects of the odour of young leaf buds. The complete absence of the fruity note and the appearance of typical flowery nuances and the prominence of the natural forest soil character are remarkable.

Tiglates have recently enjoyed increasing popularity as odorant substances. However, among them there have been found no representatives which are organoleptically comparable with the compound of formula I hereinbefore.

S. Arcander describes in "Perfume and Flavor Chemicals" (1969, Montclair NJ, USA) e.g. the following structurally analogous tiglates:

| | | |
|---|---|---|
| No. 1630: | cis-3-hexenyl tiglate | fresh, powerful, dark green leaves with slight fruity undertone. |
| No. 1631: | trans-2-hexenyl tiglate | warm-herby, green odour with slight fruity undertone. |
| No. 1682: | n-hexyl tiglate | pleasant, sweet-green, oily, herby and slightly vinous odour which is reminiscent of unripe berries or plums. |
| No. 225: | iso-amyl tiglate | pleasant herby and vinous odour, reminiscent of medicinal herbs. |
| No. 540: | n-butyl tiglate | warm-herby, diffuse, ethereal and sweet. |

Again, the olfactory comparison with 2-methyl-2-buten-1-yl 2-methylbutyrate 2, 2-methyl-butyl tiglate 3 and prenyl senecioate 4, known as an insect combating agent (Swiss Patent Specification No. 264 520, Jan. 16, 1950 and U.S. Pat. No. 2,554,947, May 29, 1951), also shows, moreover, that none of these compounds has the typical olfactory properties of 2-methyl-2-buten-1-yl tiglate of formula I and only this tiglate alone, which is reminiscent of damp forest soil, at the same time also combines in its molecule delicate-flowery and bud-like odour combinations without any fruity aspect.

| | Odour |
|---|---|
| 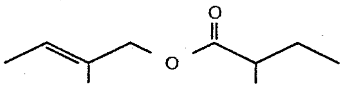 2 | ester-like, fruity, berry-like, aspects of elder. |
| 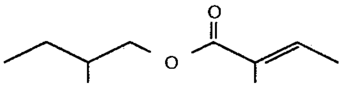 3 | herby, sweet with green and slightly fruity undertone. |
| 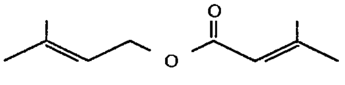 4 | warm-herby, green, chervil-like. |

The compound of formula I can therefore be used, for example, for the perfuming or flavouring of products such as cosmetics (soaps, ointments, powders, toothpastes, mouth washes, deodorants, shampoos, lotions etc), detergents, foodstuffs, luxury consumables and drinks, the compound of formula I preferably not being used alone but in the form of compositions which contain other odorant or flavouring substances. Such odorant or flavouring compositions containing the compound of formula I and their manufacture carried out in a manner known per se (addition of the compound of formula I to known odorant or flavouring compositions or mixture of the compound of formula I with natural or synthetic compounds or mixtures suitable as the ingredients of odorant or flavouring compositions) also form objects of the present invention.

On the basis of its aforementioned original notes, the compound of formula I is suitable as an odorant substance, especially in combination with a series of natural and synthetic odorant substances such as, for example:

patchouli oil, pine-needle absolute, tree moss absolute, frankincense balsam, sandalwood oil, basil oil, mugwort oil, camomile oil, sage oil, tagetes oil, ylang-ylang oil, bergamot oil, lemon oil, petitgrain oil, neroli oil etc, aldehydes such as hydroxycitronellal, α-hexylcinnamaldehyde, lauric aldehyde, methylnonylacetaldehyde, Cyclal® (2,4-dimethyl-3-cyclohexenyl-1-carboxaldehyde), citral, cyclamen aldehyde, anisaldehyde etc, ketones such as α-ionone, β-ionone, methylionone etc., acetals and ketals such as Acetal CD® (Givaudan) (phenylacetaldehyde glycerinacetal), Fructone® (2-methyl-1,3-dioxolan-2-ethyl acetate) etc, ethers such as eucalyptol, methyl p-cresol, anethol, methyl 1-methylcyclododecyl ether etc, phenolic compounds such as eugenol, isoeugenol etc, alcohols such as linalool, citronellol, geraniol, cinnamic alcohol, benzyl alcohol, phenylethyl alcohol, α-terpineol etc, esters such as linalyl acetate, bornyl acetate, vetiveryl acetate, geranyl acetate, benzyl acetate, benzyl salicylate, amyl salicylate, styrallyl acetate, phenylethyl phenylacetate, methyl dihydrojasmonate etc, lactones such as γ-nonalactone, γ-decalactone, γ-undecalactone, δ-decalactone etc, acids such as phenylacetic acid α-methylbutyric acid etc, compounds having a musk-like and amber-like odour such as ethylene brassylate, musk ketone, 8α,12-oxido-13,14,15,16-tetranorlabdane etc, sulphur-containing compounds such as p-menthane-8-thiol-3-one etc, nitrogen-containing compounds such as methyl anthranilate, linalyl anthranilate etc.

As will be evident from Examples 2–8 hereinafter, extremely interesting effects can be achieved with the compound of formula I. In addition to producing valuable and original effects in odorant compositions of the chypre, cologne, wood, jasmine or rose type or in compositions having a generally flowery direction it is, however, also possible to produce novel perfume complexes with 2-methyl-2-buten-1-yl tiglate of formula I. Thus, for example, flowery-fruity complexes from linalool and a lactone (e.g. δ-decalactone) are harmonised and enriched by an additional exotic aspect by adding 1–5% of the compound of formula I. The compound of formula I can also be used in the reconstitution of essential oils or absolutes.

In the production of such compositions the known odorant substances specified earlier can be used according to methods which are known to the perfumer such as, for example, as described by W. A. Poucher, Perfumes, Cosmetics and Soaps 2, 7th Edition, Chapman and Hall, London, 1974.

The concentration of the compound of formula I can vary within wide limits depending on the purpose of use, for example between about 0.01 wt.% in the case of detergents and about 15 wt.% in the case of alcoholic solutions. In perfume bases or concentrates the concentrations can, of course, also be higher. The perfume bases can be used in the customary manner for the perfuming of Eau de Cologne, eau de toilette, extracts, lotions, creams, shampoos, soaps, detergents etc. The use of the compound of formula I in colognes and extracts is preferred.

As a flavouring substance, the compound of formula I can be used, for example, for the production or improvement, enhancement or modification of various flavour types such as those used, for example, for the flavouring of foodstuffs (yoghurt, sweet goods, e.g. candies, etc), luxury consumables (tea etc), and drinks (lemonades etc). In particular, interesting effects in the modification of strawberry or herb tea flavours can be produced by adding the compound of formula I (see Table II hereinafter).

The pronounced flavour qualities of the compound of formula I enables it to be used in low concentrations. A suitable range is, for example, 0.1 ppm–100 ppm, preferably 1 ppm–20 ppm, in the finished product (i.e. the flavoured foodstuff, luxury consumable or drink).

In Table II hereinafter there are compiled effects which can be achieved with the compound of formula I.

TABLE II

| Flavour | Amount | Effect |
|---|---|---|
| Herb tea | ppm in the finished product 0.1–30 ppm, especially 0.5–4 ppm | More complete flavour, more character |
| Strawberry | ppm in the finished product 0.1–100 ppm, especially 1–20 ppm | Modification in the direction of cranberries |

The compound of formula I can be mixed with the ingredients used for flavouring compositions or added to such flavourants in the customary manner. Among the flavourants contemplated in accordance with the invention there are to be understood flavouring compositions which can be diluted or dispersed in edible materials in a manner known per se. The flavouring compositions provided by this invention can be converted according to methods known per se into the customary forms of use such as solutions, pastes or powders. The present flavouring compositions can be spray-dried, vacuum-dried or lyophilised.

The known flavouring substances conveniently used in the production of such flavourants are either included in the foregoing compilation or can readily be selected from the literature; for example, from J. Merory, Food Flavorings, Composition, Manufacture and Use, Second Edition, The Avi Publishing Company, Inc., Westport, Conn. 1968, or G. Fenaroli, Fenaroli's Handbook of Flavor Ingredients, Second Edition, Volume 2, CRC Press Inc., Cleveland, Ohio, 1975.

For the production of such customary forms of use there come into consideration, for example, the following carrier materials, thickening agents, flavour-improvers, spices, auxiliary ingredients etc.:

Gum arabic, tragacanth, salts or brewer's yeast, alginates, carrageen or similar absorbants; indole, maltol, spice oleoresins, smoke flavours; cloves, sodium citrate; monosodium glutamate, disodium inosine-5'-monophosphate (IMP), disodium guanosine-5-phosphate (GMP); or special flavouring substances, water, ethanol, propyleneglycol, glycerin.

The following Examples illustrate the present invention:

EXAMPLE 1

A solution of 133.6 g (1.13 mol) of tiglic acid chloride in 100 ml of toluene was allowed to drop into a solution of 106.2 g (1.24 mol) of 2-methyl-2-buten-1-ol and 172.5 g (1.43 mol) of dimethylaniline in 350 ml of toluene over a period of 30 minutes. The mixture was subsequently stirred for 16 hours at 40° C., cooled to room temperature, diluted with 200 ml of ether, washed with dilute hydrochloric acid until the excess dimethylaniline had been completely removed and then with water until neutral. After drying over sodium sulphate and concentration, there were obtained 212 g of crude compound of formula I from which 131.5 g of pure and olfactorily good compound of formula I of boiling point 92° C./12 mmHg were obtained by distillation over a 20 cm Widmer column.

Spectral data:

IR: 1715, 1265, 1255, 1155, 1138, 1072, 732 $cm^{-1}$.

NMR: 1.6–1.9 (4 $CH_3$ on double bonds, mutually overlapping)

4.58 (s, 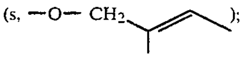 );

5.61 (m, 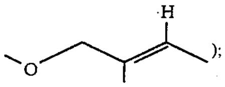 );

6.90 (m, 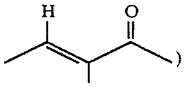 ) δ ppm

MS: 168 (M+, 2), 139 (8), 123 (8), 101 (13), 83 (100), 69 (32), 55 (55), 41 (43), 39 (23), 27 (21).

EXAMPLE 2

| Perfume base direction of chypre | Parts by weight |
|---|---|
| Bergamotte oil | 200 |
| Hydroxycitronellal | 160 |
| Linalool | 120 |
| Patchouli oil | 60 |
| β-Ionone | 60 |
| 12-Oxahexadecanolide | 60 |
| Bornyl acetate | 60 |
| Tree moss absolute | 60 |
| Lemon oil | 60 |
| Vetivenyl acetate | 60 |
| Indole (10% in ethanol) | 20 |
| Mugwort oil | 20 |
| Pine-needle balsam absolute | 10 |
| Eugenol extra | 10 |
| Rhodinol pure | 20 |
| | 980 |

If there are added to this conventional chypre composition 20 parts of the compound of formula I, then the original composition takes on a much fresher top note, the bergamotte oil is underlined advantageously and the resulting composition is more delicate and lighter.

EXAMPLE 3

-continued

| Flowery base for use in perfumery | Parts by weight |
|---|---|
| Benzyl acetate | 180 |
| Linalool | 120 |
| Isoeugenol | 100 |
| Geranyl acetate | 100 |
| Methyl benzoate | 100 |
| Geraniol | 100 |
| Linalyl acetate | 50 |
| Benzyl salicylate | 40 |
| Hydroxycitronellal | 30 |
| Amyl salicylate | 30 |
| Methylionone | 30 |
| Cinnamic alcohol | 20 |
| Musk ketone | 20 |
| Heliotropin | 5 |
| Eugenol | 5 |
| Methyl p-cresol | 5 |
| Linalyl anthranilate | 5 |
| | 960 |

If there are added to this flowery base, which tends in the direction of ylang, 40 parts of the compound of formula I, then the resulting composition is much more delicate, generally flowery and much more diffuse. This effect can be detected very well even after 24 hours.

EXAMPLE 4

| Perfumery base direction of Eau de Cologne | Parts by weight |
|---|---|
| Bergamotte oil | 404 |
| Lemon oil | 120 |
| a-Hexylcinnamaldehyde | 100 |
| Methyl dihydrojasmonate | 60 |
| α-Ionone | 60 |
| Basil oil | 50 |
| Rhodinol pure | 40 |
| Eugenol | 40 |
| Neroli oil | 40 |
| Patchouli oil | 20 |
| Tree moss absolute (50% in propyleneglycol) | 20 |
| Vetivenyl acetate | 20 |
| Ylang-ylang oil | 20 |
| | 994 |

If there are added to this Eau de Cologne 6 parts of the compound of formula I, then the resulting composition is much fresher and more powerful, and there results a very pleasant aromatic citrus peel note which is not present in the original base. With increasing concentration (1% and 2%) there results a very original and sharp effect which confers more life to the composition and makes it especially suitable for mens colognes.

EXAMPLE 5

| Perfumery base general-flowery direction | Parts by weight |
|---|---|
| Benzyl alcohol | 500 |
| Phenylethyl alcohol | 250 |
| α-Hexylcinnamaldehyde | 70 |
| Benzyl acetate | 60 |
| Linalool | 40 |
| Indole (10% in propyleneglycol) | 20 |
| Linalyl anthranilate | 10 |
| δ-Undecalactone (10% in propyleneglycol) | 10 |
| | 960 |

The addition of 40 parts of the compound of formula I to this base which has a general-flowery odour surprisingly brings about a significant modification of the odour in the direction of hyacinth. The novel modified base has more character and radiance.

EXAMPLE 6

Fresh-green base for use in perfumery

| | Parts by weight |
|---|---|
| Bornyl acetate | 200 |
| Methyl 1-methylcyclododecyl ether | 160 |
| β-Hexylcinnamaldehyde | 140 |
| Linalool | 100 |
| Frankincense balsam | 80 |
| 1,1,2,4,4,7-Pentamethyl-6-acetyl-1,2,3,4-tetrahydronaphthalene | 60 |
| α-Terpineol | 60 |
| α-Ionone | 60 |
| Styrallyl acetate | 30 |
| Linalyl anthranilate | 20 |
| Dodecanal (10% in ethanol) | 10 |
| Methylnonylacetaldehyde (10% in ethanol) | 10 |
| 3,5-Dimethyl-cyclohex-3-en-1-carbaldehyde | 6 |
| p-Menthane-8-thiol-3-one | 4 |
| Tree moss absolute | 10 |
| Citral | 20 |
| | 970 |

If there are added to this fresh-green base 30 parts of the compound of formula I, then the resulting composition is much more powerful and more natural. A very pleasant forest smell is established. The bornyl acetate is pleasantly and significantly emphasised.

EXAMPLE 7

Woody perfume base

| | Parts by weight |
|---|---|
| Phenylethyl phenylacetate | 170 |
| Phenylethyl alcohol | 100 |
| Phenylacetaldehyde glycerylacetal | 100 |
| Methyl dihydrojasmonate | 100 |
| Sandalwood oil | 120 |
| Benzyl salicylate | 120 |

-continued

Woody perfume base

| | Parts by weight |
|---|---|
| Methyl 1-methylcyclododecyl ether | 120 |
| Hydroxycitronellal | 60 |
| Ethylene brassylate | 40 |
| Linalool | 20 |
| Eugenol | 20 |
| Cyclamen aldehyde | 20 |
| | 990 |

If there is added to this base which has a generally woody direction 0.5% of the compound of formula I, then the resulting composition is pleasantly flowery and is especially suitable for delicate, especially flowery, directions with a woody bottom note. If the concentration is increased up to 2%, then the wood note likewise appears more in the foreground and it manifests itself in a very fine sandal note which is especially prominent in the bottom note.

EXAMPLE 8

Herb tea flavour

| | Parts by weight |
|---|---|
| Petitgrain oil (French) | 220 |
| Anethol | 150 |
| Camomile oil (Roman) | 120 |
| Tagetes oil | 110 |
| Eucalyptol | 100 |
| Linalyl anthranilate | 100 |
| Phenylethyl phenylacetate | 60 |
| Anisaldehyde | 60 |
| Sage oil (Dalmatian) | 20 |
| Neroli oil | 10 |
| | 950 |

The addition of 50 parts of 2-methyl-2-butenyl tiglate to the foregoing conventional herb tea flavour brings about a very pleasant rounding-off effect in that an intensified flowery note appears. Flavourwise, with the use of 50 g of a 2% solution of this flavour in glyceryl triacetate per 100 liters of sugar syrup 65° Bx, diluted with water in the ratio 1:5, there is likewise ascertainable a significant improvement in that, in comparison with a blind sample, the tea is now more rounded-off and, moreover, by virtue of an additional flowery note, is reminiscent of certain kinds of black tea.

What is claimed is:

1. Substantially pure 2-methyl-2-buten-1-yl tiglate.

* * * * *